(12) United States Patent
Galdonik et al.

(10) Patent No.: US 8,052,714 B2
(45) Date of Patent: **\*Nov. 8, 2011**

(54) RADIOPAQUE FIBERS AND FILTRATION MATRICES

(75) Inventors: Jason A. Galdonik, Hanover, MN (US); Matthew F. Ogle, Fitchburg, WI (US); Bruce W. Ebner, Shorewood, MN (US)

(73) Assignee: Medtronic Vascular, Inc., Santa Rosa, CA (US)

( \* ) Notice: Subject to any disclaimer, the term of this patent is extended or adjusted under 35 U.S.C. 154(b) by 473 days.

This patent is subject to a terminal disclaimer.

(21) Appl. No.: 11/603,315

(22) Filed: Nov. 21, 2006

(65) Prior Publication Data

US 2007/0172526 A1    Jul. 26, 2007

Related U.S. Application Data

(60) Provisional application No. 60/739,068, filed on Nov. 22, 2005.

(51) Int. Cl.
*A61M 29/00* (2006.01)
(52) U.S. Cl. ........................................................ 606/200
(58) Field of Classification Search .................. 606/191, 606/198, 200; 604/104–109
See application file for complete search history.

(56) References Cited

U.S. PATENT DOCUMENTS

| | | | |
|---|---|---|---|
| 4,456,706 A | 6/1984 | Siedenstrang et al. | |
| 4,550,126 A | 10/1985 | Lorenz et al. | |
| 4,842,792 A | 6/1989 | Bagrodia et al. | |
| 5,171,232 A | 12/1992 | Castillo et al. | |
| 5,200,248 A * | 4/1993 | Thompson et al. | 428/131 |
| 5,277,976 A * | 1/1994 | Hogle et al. | 428/397 |
| 5,423,849 A | 6/1995 | Engelson et al. | |
| 5,458,963 A | 10/1995 | Meirowitz et al. | |
| 5,509,044 A | 4/1996 | Horbaschek | |
| 5,810,874 A * | 9/1998 | Lefebvre | 606/200 |
| 5,836,962 A * | 11/1998 | Gianotti | 623/1.51 |
| 5,914,125 A | 6/1999 | Andrews et al. | |
| 5,928,260 A * | 7/1999 | Chin et al. | 606/200 |
| 6,013,084 A * | 1/2000 | Ken et al. | 606/108 |
| 6,146,396 A * | 11/2000 | Konya et al. | 606/159 |
| 6,165,198 A * | 12/2000 | McGurk et al. | 606/200 |
| 6,320,011 B1 | 11/2001 | Levy et al. | |

(Continued)

FOREIGN PATENT DOCUMENTS

WO    WO 01/45590 A2    6/2001

(Continued)

OTHER PUBLICATIONS

Jayakrishman et al., "Synthesis and Polymerization of Some Iodine-Containing Monomers for Biomedical Applications", J. of Applied Polymer Science, vol. 44, No. 4, Feb. 5, 1992, pp. 743-748.

(Continued)

*Primary Examiner* — S. Thomas Hughes
*Assistant Examiner* — David Eastwood (57) ABSTRACT

Medical devices with radiopaque three dimensional filtration matrices provide for improved visualization of the device within a vessel. In some embodiments, the three dimensional filtration matrix comprises fibers, such as surface capillary fibers. Visualization of the three dimensional filtration matrix provides for an evaluation of the proper deployment of the three dimensional filtration matrix. Radiopaque surface capillary fibers can be advantageously incorporated into other medical devices. Radiopaque surface capillary fibers can be formed by extrusion of a radiopaque polymer or polymer composite.

9 Claims, 6 Drawing Sheets

U.S. PATENT DOCUMENTS

| | | | |
|---|---|---|---|
| 6,383,205 B1 * | 5/2002 | Samson et al. | 606/200 |
| 6,475,477 B1 | 11/2002 | Kohn et al. | |
| 6,514,734 B1 | 2/2003 | Clapper et al. | |
| 6,599,308 B2 * | 7/2003 | Amplatz | 606/200 |
| 6,616,617 B1 | 9/2003 | Ferrera et al. | |
| 6,758,855 B2 * | 7/2004 | Fulton et al. | 606/200 |
| 6,761,727 B1 * | 7/2004 | Ladd | 606/200 |
| 6,783,538 B2 * | 8/2004 | McGuckin et al. | 606/200 |
| 6,793,665 B2 * | 9/2004 | McGuckin et al. | 606/200 |
| 7,077,837 B2 | 7/2006 | Sahagian | |
| 2001/0044632 A1 | 11/2001 | Daniel et al. | |
| 2002/0058988 A1 * | 5/2002 | Fischell et al. | 623/1.15 |
| 2002/0072550 A1 | 6/2002 | Brady et al. | |
| 2002/0072730 A1 | 6/2002 | McGill et al. | |
| 2004/0054413 A1 | 3/2004 | Higham et al. | |
| 2004/0093015 A1 | 5/2004 | Ogle | |
| 2004/0122466 A1 * | 6/2004 | Bales | 606/200 |
| 2004/0142016 A1 | 7/2004 | Luthra et al. | |
| 2004/0193208 A1 | 9/2004 | Talpade et al. | |
| 2004/0220611 A1 * | 11/2004 | Ogle | 606/200 |
| 2005/0010245 A1 * | 1/2005 | Wasicek | 606/200 |
| 2005/0021152 A1 | 1/2005 | Ogle et al. | |
| 2005/0031539 A1 | 2/2005 | Sugiyama et al. | |
| 2005/0085847 A1 | 4/2005 | Galdonik et al. | |
| 2005/0277976 A1 | 12/2005 | Galdonik et al. | |
| 2006/0200047 A1 | 9/2006 | Galdonik et al. | |

FOREIGN PATENT DOCUMENTS

WO      WO 01/45590 A3      6/2001

OTHER PUBLICATIONS

Kruft et al., "Studies on Radio-Opaque Polymeric Biomaterials With Potential Applications to Endovascular Prostheses", Biomaterials, vol. 17, No. 18, Sep. 1996, pp. 1830-1812.

* cited by examiner

RADIOPAQUE FIBERS AND FILTRATION MATRICES

CROSS REFERENCE TO RELATED APPLICATIONS

This application claims priority to provisional U.S. patent application Ser. No. 60/739,068 filed on Nov. 22, 2005 to Galdonik et al., entitled "Radiopaque Fibers and Filtration Matrices," incorporated herein by reference.

FIELD OF THE INVENTION

The invention relates to three dimensional filtration matrices formed from a radiopaque material, such as a polymer composite. In addition, the invention relates to methods for delivery of a filter within a vessel of a patient and visualizing the contact of the filter with the vessel walls. The invention further relates to biocompatible fibers formed with a radiopaque polymer, which can be incorporated, for example, into various medical devices.

BACKGROUND OF THE INVENTION

A variety of medical procedures are performed with less invasive approaches to reach distant locations within a patient's body. These procedures can be used, for example, for entry into the abdominal cavity or into the urinary track, or for reaching the patient's genitals. However, many of the procedures are performed within the cardiovascular system. For any of these procedures, a guidewire can be used to snake through the patient to position the tip of the guidewire at a desired location. A catheter and/or other medical devices can be positioned by sliding them over the guidewire to the appropriate location. Visualization techniques may be important since the physician generally cannot directly see the intervention site within the patient. X-rays can be used in the visualization technique due to their penetrative ability. Visualization then is based on using materials that are not transparent to x-rays so that the x-rays produce a discernable image.

Generally, to position the guidewire, the guidewire traverses along a pathway, such as through vessels of the cardiovascular system, that generally has bends and branches. To navigate along the curves and branches, the guidewire and catheters are flexible and to some degree steerable. Through the application of torque, the tip can be guided along a selected path within the patient. Generally, a portion of the guidewire at or near the tip is formed from a radiopaque material to provide for identification of the tip position. As further devices are delivered to the intervention site, these other devices generally also have a radiopaque portion that provides for some degree of visualizing the position of the device.

Many less invasive procedures create the possibility of emboli formation as a result of the procedure. Also, some procedures may be specifically initiated to capture and/or remove emboli, which have been generated or have a risk of being generated as a result of a procedure, injury and/or disease. An embolus can be any particle comprising a foreign and/or native material, which enters the vascular system or other vessel of the body with potential to cause occlusion of flow, e.g., blood flow. Emboli can be formed from aggregates of fibrin, blood cells or fragments thereof, collagen, cholesterol, plaque, fat, calcified plaque, bubbles, arterial tissue, and/or other miscellaneous fragments or combinations thereof.

Emboli can lodge, for example, in the narrowing regions of medium size blood vessels that feed the major organs. Loss of blood flow to surrounding tissue can cause localized cell death or microinfarcts. Cerebral microinfarcts can cause stroke leading to confusion, disturbance of speech, paralysis, visual disturbances, balance disturbances and even death. In the heart, emboli can cause myocardial infarcts, i.e. heart attacks. Myocardial infarction refers to the death of a section of myocardium or middle layer of the heart muscle. Myocardial infarction can result from at least partial blockage of the coronary artery or its branches. Blockage of capillaries associated with the coronary arteries can result in corresponding microinfarctions/microinfarcs. Resulting impairments are frequently short term but can be permanent.

Many clinical procedures can result in emboli including, for example, coronary, carotid, and peripheral interventions. In these cases, particulate matter, including, for example, plaque, debris and thrombus, can form emboli distal to the site of intervention. As a result, blood flow to the distal vascular bed can be diminished and periprocedural end-organ ischemia and infarction can result. Distal embolization of large particles produced at the time of such interventions as balloon inflation or stent deployment may obstruct large, epicardial vessels, and smaller particles (as small as 15-100 microns) can cause microinfarcts and/or myocardial infarctions and left ventricular dysfunction.

A significant reason for ischemic injury during percutaneous procedures can be generation of emboli that block smaller distal vessels. One approach to curb this complication has been to use pharmacological therapies during the time of the intervention. Limited therapeutic success has been reported with the use of calcium channel blockers, adenosine, and sodium nitroprusside (Webb, J G, Carere, R G, Virmani, R, Baim, D, Teirstein, P S, Whitlow, P, McQueen, C, Kolodgie, F D, Buller, E, Dodek, A, Mancini, G B, & Oesterle, S: Retrieval and analysis of particulate debris after saphenous vein graft intervention. *J Am Coll Cardiol* 2000, 34:468-475, incorporation herein by reference.). Glyoprotein IIb/IIIa inhibitors have been used for percutaneous coronary interventions to reduce platelet aggregation, but also fail to show meaningful long term clinical benefit. (Mathew, V, Grill, D E, Scott, C G, Grantham, J A, Ting, H H, Garratt, K N, & Holmes, D R, Jr. The influence of abciximab use on clinical outcome after aortocoronary vein graft interventions. *J Am Coll Cardiol* 1999, 34:1163-1169 and Mak, K H, Challapalli, R, Eisenberg, M J, Anderson, K M, Califf, R M, & Topol, E J: Effect of platelet glycoprotein IIb/IIIa receptor inhibition on distal embolization during percutaneous revascularization of aortocoronary saphenous vein grafts. EPIC Investigators, Evaluation of IIb/IIIa platelet receptor antagonist 7E3 in Preventing Ischemic Complications. *Am J Cardiol* 1997, 80:985-988, both of which are incorporated herein by reference.) However, since embolization often develops from physical disruption of fibrotic plaque, a mechanism of therapeutic embolic protection specifically targeted at prevention of platelet aggregation and blood clotting may have little effect on these already-formed, embolizable plaques.

SUMMARY OF THE INVENTION

In a first aspect, the invention pertains to a medical device comprising a three dimensional filtration matrix having a deployment configuration with a relatively low profile relative to an axis and a filtering configuration with a relatively large profile relative to the axis. The three-dimensional filtration matrix comprising a radiopaque material.

In another aspect, the invention pertains to a filtration device comprising a guide structure and a filter element comprising a radiopaque composition operably connected to the guide structure. The filter element having a delivery configuration and a deployed configuration with a profile that extends outward from the guide structure relative to the delivery configuration. The filter element has an x-ray image in its deployed configuration with a peak intensity greater than the peak intensity of the x-ray image in its delivery configuration when the x-ray source is oriented perpendicular to the axis aligned through the center of the vessel at the filter.

In a further aspect, the invention pertains to a method for filtering flow within a vessel of a patient. The method comprises visualizing the interface of an embolism protection device with the vessel to determine if the filter is properly deployed. The embolism protection device comprises a three dimensional filtration matrix.

In another aspect, the invention pertains to a medical device comprising a surface capillary fiber comprising a biocompatible, radiopaque material.

In other aspects, the invention pertains to a method for forming a radiopaque biocompatible fiber. The method comprises extruding a radiopaque, biocompatible material to form a fiber, the radiopaque, biocompatible material comprising a polymer.

DETAILED DESCRIPTION OF THE INVENTION

Filters for vessels within a patient can be formed from a three dimensional filtration matrix that is radiopaque. Having a radiopaque filtration matrix provides for visualization of the interaction of the filter material with the vessel wall to evaluate both location of the deployed filter and proper configuration of the deployed filter. In embodiments of particular interest, the device is an embolism protection device in which a bundle of fibers form a filter when deployed within a vessel. Other three dimensional filtering matrices can be formed from radiopaque polymer materials suitable for deployment in a vessel. In addition, radiopaque fibers can be formed into other medical devices to facilitate visualization. Radiopaque fibers can be formed, for example, by extruding a filled polymer material. In some embodiments, the radiopaque fibers have surface capillaries. In general, for visualization of the fibers following placement within a patient, it may be desirable to have a collection of the fibers within the device such that a cross section through the device involves more than a single thickness of fiber. The radiopaque material provide for significantly improved visualization of the filter deployment and contact with the vessel walls to provide a check on proper deployment.

Filter elements can trap emboli that are flowing through the vessel to prevent distal migration of the emboli. Filter elements can be used as embolism protection devices during procedures within a vessel. Three dimensional filtration matrices have the advantage that alternative flow paths are available such that good flow is maintained through the filter even following moderate loading of the device with emboli. In particular, filters with three dimensional filtration matrices generally can be used with little or no pressure drop across the filter when deployed. This performance of the filters with three dimensional filtration matrices is in contrast with conventional embolism protection devicess in which filtration is provided by a filter membrane, which have greater pressure drops and are more susceptible to clogging.

Inherently, filters with membranes are somewhat occlusive in comparison with filters with three-dimensional filtration matrices, since filtration membranes rely on reductions of the flow to capture emboli. Also, once emboli block pores in a filter membrane, the effective surface area of the flow is correspondingly reduced further. Using a wind sock shape for the filter membrane can alleviate somewhat flow restrictions resulting from the trapping of emboli in the membrane by increasing the surface area of the device, but such designs introduces other disadvantages related to spatial extent within the vessel. Due to the larger longitudinal extent of such filters, membrane-based filters cannot be placed at certain desirable locations within a vessel.

A three dimensional filtration matrix provides excellent flow through the filter and a high collection capacity for emboli while maintaining a small spatial extent within the vessel. Filters with three-dimensional hydrogel filtration matrices are discussed further, for example in published U.S. Patent Application 2004-0093015A to Ogle, entitled "Embolism Protection Devices," incorporated herein by reference. However, extremely effective embolism protection devices have been designed based on fibers that form three dimensional filtration matrices.

In particular, desirable embolism protection structures can be formed using filtering media with a three dimensional filtering matrix provided by a flared bundle of fibers. A fiber-based embolism protection component connected to an integrated guiding device is described further below. In this device, the fibers are attached at one end to a corewire and at the other end to an overtube, e.g., a hypotube. The device can be deployed with the fibers aligned in a low profile configuration. Upon longitudinal pulling of the corewire proximal relative to the overtube, the fibers flare outward to a deployed configuration in which the device can provide filtering within a patient's vessel. Reversal of the longitudinal motion of the corewire relative to the tube can unbend the fibers to a removal configuration. Fiber-based embolism protection devices are described further in published U.S. Patent Application 2006/0200047A to Galdonik et al., entitled "Steerable Device Having a Corewire Within a Tube and Combination With a Functional Medical Component," incorporated herein by reference. Aspiration can be applied during the removal of the device, as described further in published U.S. Patent Application 2005/0277976A filed May 27, 2004 to Galdonik et al., entitled "Emboli Filter Export System," incorporated herein by reference.

In general, the fibers can have circular cross sections or non-circular cross sections, such as an oval cross section. In some embodiments, the fiber-based embolism protection device comprises surface capillary fibers. In vitro flow experiments indicate that embolism protection devices formed with surface capillary fibers (SCF fibers) provide excellent filtering properties. In addition, human clinical trials have been performed with these devices with a high approval rating of the performance. Embolism protection devices with SCF fibers are described further in published U.S. Patent Application 2005/0085847A filed Mar. 6, 2004 to Galdonik et al., entitled "Fiber Based Embolism Protection Device," incorporated herein by reference.

SCF fibers are characterized by surface channels or capillaries formed along the surface of the fiber. Surface capillaries are characterized by having a portion of the capillary exposed at the surface of the fiber along the length of the fiber. The surface capillaries result in significant increase in the surface area of the fibers relative to fibers with a smooth surface and the same diameter. The surface capillaries generally run along the length of the fiber. In some embodiments, the surface of the fiber has a plurality of surface channels or capillaries along the length of the fiber. An SCF fiber can have surface channels that essentially make up a large fraction of the bulk of the fiber such that little if any of the interior mass of the fiber is not associated with walls of one or more surface capillaries.

In particular, the SCF fiber substrate can be formed with a relatively complex cross-sectional geometry. In some embodiments, the geometry of the fibers used in particular medical devices have surface capillaries that can move relatively large amounts of fluid at significant rates. Suitable fibers include commercially available 4DG™ fibers but would also include new advanced geometries to provide for greater fluid transport or absorption or wetting capabilities. In particular, geometries can be selected to be particularly advantageous for the particular application. Suitable approaches for the manufacture of the SCF fibers are described in, for example, U.S. Pat. No. 5,200,248 to Thompson et al., entitled "Open Capillary Structures, Improved Process For Making Channel Structures And Extrusion Die For Use Therein," incorporated herein by reference. Alternative fiber structures are described below.

It has been discovered that the twisting of a fiber bundle, such as an SCF fiber bundle, in an embolism protection device can assist with keeping the fibers free of gaps during deployment and can result more consistent performance of the filter following deployment in a patient. Rotationally locking the tube to the corewire allow for the fiber bundle to be twisted and for the twist to be preserved through sterilization and final use of the device. In some embodiments, gentle heat can be added during the manufacturing process to impart a shape memory into the polymer, although heat is not required for consistent performance of the device or for elimination of gaps in the deployed fibers.

The radiopaque materials of particular interest generally comprise a polymer. In some embodiments, the polymer is directly formed as a radiopaque composition. However, in other embodiments, the polymer is loaded with a particulate radiopaque composition to form a radiopaque composite material. In some embodiments, the radiopaque polymers can be substituted into device designs in which the radiopaque polymer substitutes for a x-ray transparent polymer. For these embodiments, the radiopaque polymers should have physical properties similar to the x-ray transparent polymers.

A three dimensional filtration matrix comprising a radiopaque material provides for valuable visualization through the space filling filtration matrix. In other words, the visualization techniques project the view of the three dimensional material onto a plane. Even though the filtration matrix is not dense since it can provide for effectively unrestricted flow through the matrix, the mass along a cross section through the filter provides for an effective thickness of material that results in good visualization. The imaging process involves the projection of x-rays through the material to film or other detector, in which the image is formed through the blockage through absorption or scattering of the x-rays. Since each point of the image corresponds with the trajectory of a ray of x-ray radiation, any point of the image corresponds with a look through the thickness of the matrix.

In contrast, an image through a filter membrane only looks through one or two layers of the membrane. The filter membrane generally is thin so that the filter structure can be reasonably delivered to the site. Since the image is formed by two thin layers of the filter membrane, a larger and much more diffuse image results with corresponding lower image quality.

Similarly, the filter with a three dimensional filtration matrix generally has a low profile delivery configuration. In some embodiments, upon deployment, the filtration matrix expands across the vessel and contracts in longitudinal extent along the vessel. Generally, it is desirable to position the patient so that the x-ray imaging is done across the vessel. As the filter is deployed, the filtration matrix expands and fills a region of the vessel being viewed. This change in configuration generally increases the focal density of the radiopaque material in the vessel from the plane in which it is viewed. This change in effective density for viewing allows less radiopacifier to be added to the material while maintaining visibility; and thus the mechanical properties of the composite can be better preserved relative to the unfilled polymer. Furthermore, the physician can rely on both the change in configuration of the filter matrix and the change in contrast to indicate that the filter has been properly deployed.

Additionally or alternatively to the use of a radiopaque three dimensional filtration matrix, the devices can comprise radiopaque markers separate from the filtration matrix itself.

For example, radiopaque bands can be placed at or near the respective ends of fiber bundles attached to an integrated guide device. When the corewire is moved relative to the overtube, the fibers flare outward, and the two marker bands move towards each other and can be designed to overlap such as with extending arms, when the filter element is fully deployed. Furthermore, separate radiopaque elements can be combined with the filtration matrix. For example, tungsten or other radiopaque wires can be combined in polymer fibers to form the filtration matrix. The metal wires, which can be of similar dimensional as polymer fibers in the bundle, contribute in a minor way to the filtration properties of the matrix, but can contribute significantly to the radiopacity of the three dimensional filtration matrix. In these embodiments with thin metal wires, polymer fibers within the fiber bundle may or may not also be formed with a radiopacifier. In this way, the radiopaque properties of the three dimensional filtration matrix can be enhanced without significantly altering the filtration properties.

Figures 1A, 1B, 2:
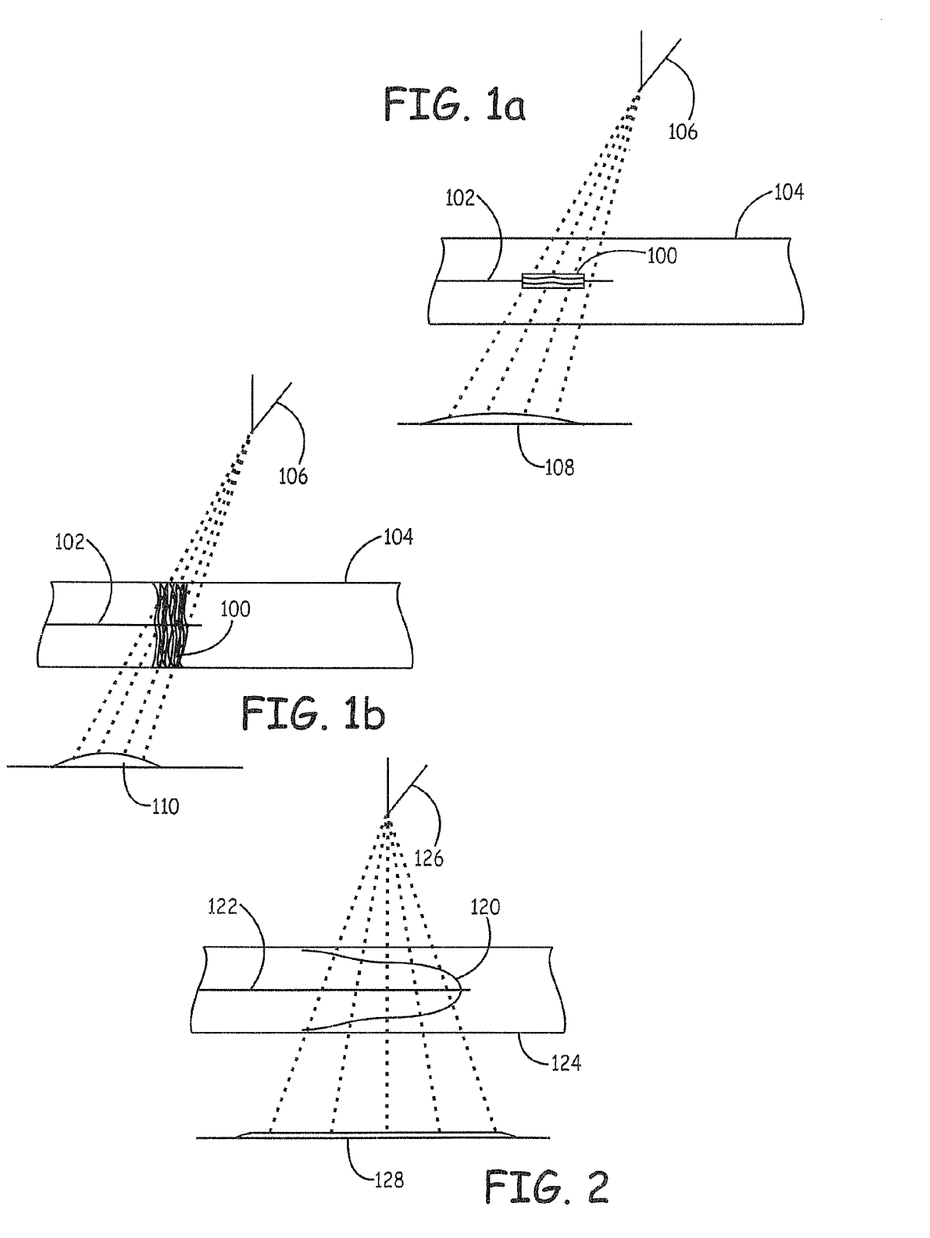
FIG. 1a is a schematic view depicting an x-ray image formed with an embolic protection device in a delivery configuration in a patient's vessel in which the embolic protection device has a three-dimensional filtration matrix following deployment.
FIG. 1b is a schematic view depicting an x-ray image formed with an embolic protection device deployed in a patient's vessel in which the embolic protection device has a three-dimensional filtration matrix.
FIG. 2 is a schematic view depicting an x-ray image formed with an embolic protection device deployed in a patient's vessel in which the embolic protection device has a conventional filtration membrane.

Referring to FIG. 1a, a filter 100 with a three dimensional filter matrix in a low profile delivery configuration is attached to a guidewire 102 or other tether within vessel 104. Similar filters can be deployed without a tether. An x-ray emitter 106 projects x-rays to form an image 108 of filter 100. The absorption and/or scattering of the x-rays is a function of the amount of radiopaque material along a ray of x-ray projection so that less exposure at the image results if there is more radiopaque material, as shown schematically in image 108. Referring to FIG. 1b, filter 100 is shown with the filtration matrix in a deployed configuration. In this configuration, filter 100 projects a more intense but smaller image. Thus, an image with higher contrast results if portions of the x-ray image result from imaging a greater density of radiopaque material along an x-ray path.

Referring to FIG. 2, a filter membrane 120 is attached to a guidewire 122 or other tether within a vessel 124. X-ray emitter 126 projects x-rays to form an image 128 of filter membrane 120. Filter membrane 120 may have a longer longitudinal extent along vessel 124 relative to a filter with a three dimensional filtration matrix since it can be desirable to increase the surface area of the filter membrane to prevent excessive pressure drops or blockage of the membrane. Generally, each point of image 128 results from x-ray transmission through two layers of filter membrane. Since the filter membrane should be relative thin to allow reasonable deployment and filtering within a vessel, the resulting image can be large but with low contrast. Therefore, the image quality is significantly lower in image 128 in comparison with the image quality in image 108. The image resulting in FIG. 2 has much less contrast than the image in FIG. 1, which provides a surprising improvement in usefulness of the imaging process.

In summary, the formation of filtration membrane of a radiopaque material generally does not yield a clear image since the image only looks through two thicknesses of filtration membrane. Such an embodiment is described in published U.S. Patent Application 2004/0193208A to Talpade et al., entitled "Radiopaque Embolic Protection Filter Membrane," incorporated herein by reference. Adding higher and higher concentrations of radiopaque composition into the membrane material to improve the quality of the imaging can result in significant changes to the material properties that produce a material with undesirable properties while not qualitatively improving the image quality. In contrast, the embodiments described herein generally provide a suitable image of the filtration matrix within the vessel wall such that the proper deployment of the filter matrix can be visually verified using x-ray techniques, which is not feasible with a low contrast image. Furthermore, if contrast is deployed within the vessel, the vessel walls can be observed so that the proper interaction of the filter with the vessel wall can be verified. This evaluation of the filter deployment can be facilitated in some embodiments by the change in image of the filter when the filter is deployed from a low profile delivery configuration.

In general, the radiopaque polymers can be processed using various polymer processing techniques, such as molding, extruding and the like. For the formation of fibers, generally an extrusion process is suitable. As described below, a die can be selected to yield the desired fiber parameters. In particular, extrusion can be used to form surface capillary fibers.

The embolism protection devices can be used to collect debris formed in a procedure performed in the vessel. In general, the filter is placed up stream from the site of the therapeutic procedure. Suitable procedures include, for example, angioplasty procedures and stent delivery. The procedures described herein are generally used on mammalian patients, in particular humans, farm animals or pets.

In general, embolism protection devices with three dimensional filtration matrices have shown great potential as improved vascular filtration devices in human clinical trials. In particular, devices based on a bundle of SCF fibers mounted on an integrated guide structure have demonstrated ease of use, relative low cost, great effectiveness even for carotid procedures, and significant versatility. The ability to provide improved visualization in the use of these devices provides an added surprising advantage to these devices. Furthermore, the ability to provide radiopaque fibers for other medical device applications can provide added versatility to a range of designs for medical devices.

Radiopaque Compositions and Fiber Properties

The radiopaque three dimensional filtration matrices can be formed from radiopaque polymers that are formed into a porous structure or formed into fibers that are assembled into a structure to form the matrix. The radiopaque fibers can be formed into other medical devices as appropriate. For example, other medical devices incorporating SCF fibers are described in published U.S. Patent Application 2005/0021152A to Ogle et al., entitled "Medical Articles Incorporating Surface Capillary Fiber," incorporated herein by reference. In general, the fibers can have an approximately circular cross section or a non-circular cross section.

In general, the materials that contact the patient's bodily fluids and tissues are biocompatible. Biocompatible materials generally are non-toxic, non-carcinogenic and blood compatible and do not induce hemolysis or a significant immunological response. In general, the devices described herein can comprise various materials for the particular components. Suitable biocompatible materials generally include, for example, metals, such as stainless steel or alloys, e.g., Nitinol®, or polymers such as polyether-amide block co-polymer (PEBAX®), nylon (polyamides), polyolefins, polytetrafluoroethylene, polyesters, polyurethanes, polycarbonates or other suitable biocompatible polymers. In particular, we consider the composition of fibers for incorporation into an embolism protection device.

The fibers can have a non-circular cross section, such as an oval cross section or other shape. As used herein, SCF fibers refer broadly to fibers having channels or capillaries along the surface running generally along the length of the fiber or a portion thereof. Fibers have their usual meaning as structures with a length that is significantly larger than the dimensions along a cross section perpendicular to the length, generally with an aspect ratio of at least about 10. The capillaries can run along substantially the entire length of the fiber or a fraction thereof.

Figure 3:
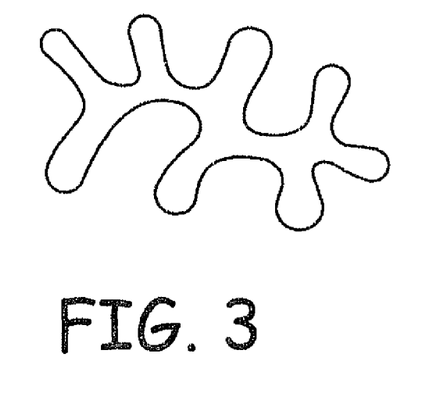
FIG. 3 is a sectional view of an embodiment of a surface capillary fiber.

Due to the presence of the capillaries, a cross section through the fiber at the capillary(ies) has a shape with an edge having changing curvatures. A representative cross sectional shape is shown schematically in FIG. 3, although any of wide range of cross sectional shapes are suitable as long as a surface capillary is formed. As shown schematically in FIG. 3, the fiber has eight surface capillaries.

Compositions for radiopaque three dimensional filtering matrices and, in general, radiopaque fibers for any type of medical device generally comprise biocompatible polymers. The radiopaque property of the fibers can be introduced by using a radiopaque polymer or by loading a polymer with radiopaque particles. Radiopaque polymers include, for example, iodinated and brominated polymers, as described for example in U.S. Pat. No. 6,475,477 to Kohn et al., entitled "Radio-Opaque Polymer Biomaterials," incorporated herein by reference as well as in Kruft et al., "Studies on Radio-Opaque Polymeric Biomaterials With Potential Applications to Endovascular Prostheses," Biomaterials 17 (18): 1803-1812 (September 1996) and Jayakrishnan et al., "Synthesis and Polymerization of Some Iodine-Containing Monomers for Biomedical Applications," J. of Applied Polymer Science 44 (4) 743-748 (Feb. 5, 1992). Radiopaque polymers can be blended and/or copolymerized and/or crosslinked with non-radiopaque monomers/oligomers/polymers.

Suitable radiopaque polymer composites can comprise one or more polymers blended with one or more types of radiopaque particles, such as inorganic particles. The loading of radiopaque compositions, generally particulates, into a polymer matrix to form a radiopaque composite provides additional flexibility with respect to properties of the resulting radiopaque polymeric materials. Radiopacity can be achieved with the addition of markers, such as platinum-iridium or platinum-tungsten or through radio-pacifiers, such as barium sulfate, bismuth trioxide, bismuth subcarbonate, powdered tungsten, powdered tantalum or the like, added to a polymer.

Generally, the composite radiopaque material comprises no more than about 60 weight percent radiopaque composition, in further embodiments from about 0.5 weight percent to about 50 weight percent, in additional embodiments from about 2 weight percent to about 40 weight percent and in other embodiments from about 3 weight percent to about 30 weight percent radiopaque composition relative to the composite. Similarly, the radiopaque composite generally comprises at least about 35 weight percent polymer, in further embodiments from about 50 weight percent polymer to about 99 weight percent polymer and in other embodiments from about 60 weight percent polymer to about 98 weight percent polymer. A person of ordinary skill in the art will recognize that additional ranges of radiopaque composition concentration and polymer concentrations within the explicit ranges above are contemplated and are within the present disclosure.

Composites with lower loading of radiopaque particles are more likely to have desired degrees of flexibility and other physical properties for use in medical devices delivered into a patient through less invasive techniques. Since a denser section of material can be imaged, the configuration of three dimensional filtration matrices in general provide for lower particles loadings, desirable physical properties of suitable composites while achieving appropriate levels of visualization that provide for viewing the interface of the filter with the vessel wall. Thus, the three dimensional filter matrices combine better visualization with the capability of lower loadings with a corresponding ability to obtain desirable material properties.

In general, for filters formed from particle loaded polymers, the resulting composite should have appropriate physical properties, which in some embodiments implies that the composite has similar physical properties as the unloaded polymer. In some embodiments, having smaller average particle sizes and relatively uniformly distributed particles throughout the polymer can facilitate forming a composite with desired properties. In some embodiments, radiopaque particles have an average particle size no more than about 10 microns, in other embodiments no more than about 5 microns and in further embodiments from about 100 nm to about 2 microns. Grinding, such as bead mill grinding and the like, can be used to reduce the particle sizes for certain materials. A person of ordinary skill in that art will recognize that additional ranges of average particle sizes within the explicit ranges above are contemplated and are within the present disclosure.

Polymer binders for radiopaque composites can be fabricated from synthetic polymers as well as purified biological polymers and combinations thereof. These polymers can be loaded with the radiopaque compositions noted above. Suitable synthetic polymers include, for example, polyamides (e.g., nylon), polyesters (e.g., polyethylene teraphthalate), polyacetals/polyketals, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. Based on desirable properties and experience in the medical device field, suitable synthetic polymers include, in particular, polyether ether ketones, polyacetals, polyamides (e.g., nylons), polyurethanes, polytetrafluoroethylene, polyester teraphthalate, polycarbonates, polysulfone and copolymers and mixtures thereof.

Bioresorbable synthetic polymers can also be used such as dextran, hydroxyethyl starch, derivatives of gelatin, polyvinylpyrrolidone, polyvinyl alcohol, poly[N-(2-hydroxypropyl) methacrylamide], poly(hydroxy acids), poly(epsilon-caprolactone), polylactic acid, polyglycolic acid, poly(dimethyl glycolic acid), poly(hydroxy butyrate), and similar copolymers. Based on experience in the medical field, suitable resorbable polymers include, in particular, polylactic acid, polyglycolic acid, and copolymers and mixtures thereof.

Appropriate polymers also include biological polymers. Biological polymers can be naturally occurring or produced in vitro by fermentation and the like. Suitable biological polymers include, without limitation, collagen, elastin, silk, keratin, gelatin, polyamino acids, cat gut sutures, polysaccharides (e.g., cellulose and starch) and mixtures thereof. Biological polymers generally are bioresorbable, although the bioresorbable nature of the material may not be particularly relevant on the time scales of the use of the device. Purified biological polymers can be appropriately formed into a polymer material for further processing into fibers.

The fibers can be used as formed, or in alternative embodiments, the fibers can be coated with materials to change the surface properties. For example, the fibers can be coated with compositions that alter the hydrophilic properties of the fiber and/or to increase the biocompatability of the fiber. For example, a heparin coating can be applied to the fiber to reduce risk of clotting since heparin is a widely used anticoagulant. Suitable coating methodologies include, for example, the process described in Published U.S. Patent Application 2004/0142016A to Luthra et al., entitled "Polysaccharide Biomaterials and Methods of Use Thereof," and U.S. Pat. No. 6,514,734 to Clapper et al., entitled "Polybifunctional Reagent Having a Polymeric Backbone and Latent Reactive Moieties and Bioactive Groups," both of which are incorporated herein by reference. Also, radiopaque coatings can be applied to the fibers as an addition or an alternative to the formation of the fibers from a radiopaque composition. For example, metals, such as gold, platinum, tantalum, titanium, tungsten and the like, can be deposited as a radiopaque coating, as described further in U.S. Pat. No. 7,077,837 to Sahagian, entitled Multi-Layered Radiopaque Coating on Intravascular Devices," incorporated herein by reference. These coatings should be suitable for forming three dimensional filtration matrices. In general, the coating can be applied to an SCF fiber without destroying the surface capillary properties or otherwise adversely affecting the mechanical properties of the fiber.

A suitable length of the fibers generally depends on the specific use of the fiber. In a broad sense, the fibers generally range in size from about 500 microns to about 10 centimeters in length, although lengths outside this range are also contemplated. Also, in general, fibers have a large aspect ratio, which is the ratio of the length of the fiber to its width, with a value typically of at least about 3. Aspect ratios can be at least about 10 in some embodiments, in further embodiments at least about 25, in-other embodiments at least about 50, and in additional embodiments from about 100 to about 1000. Similarly, the capillaries generally have a length along the fiber surface that is at least a factor of three greater than the width of the capillary. In some embodiments, the surface capillaries extend along at least about 5 percent of the fiber length, in further embodiments at least about 20 percent, in further embodiments at least about 40 percent and in other embodiments at least about 60 percent. In some embodiments, the surface capillaries extend substantially along the entire length of the fiber. A person of ordinary skill in the art will recognize that additional ranges of fiber length, aspect ratio and capillary channel extent are contemplated and are within the present disclosure. In particular, one or both ends of the fiber may have different properties or no surface capillaries in some embodiments.

The properties of the surface channels and the corresponding shape of the cross-section of the fiber generally depend on the process used to form the fibers. U.S. Pat. No. 4,842,792 to Bagrodia et al., entitled "Drafting Process For Preparing A Modified Polyester Fiber," incorporated herein by reference, describes one approach for forming a fiber with a continuous surface "groove" that runs along the length of the fiber. The process in the '792 patent forms the groove starting from a conventional fiber. Another form of shaped fibers is described in U.S. Pat. No. 5,277,976 to Hogle et al., entitled "Oriented Profile Fibers," incorporated herein by reference. Other shaped fibers notches or channels are described in U.S. Pat. No. 5,458,963 to Meirowitz et al., entitled "Nonwoven Web Containing Shaped Fibers," incorporated herein by reference. Fibers with fairly complex surface channel geometry are described in U.S. Pat. No. 5,972,505 to Phillips et al., entitled "Fibers Capable Of Spontaneously Transporting Fluids," incorporated herein by reference. A further approach for forming a fiber with surface capillaries is described in U.S. Pat. No. 5,200,248 to Thompson et al. (hereinafter the '248 patent), entitled "Open Capillary Channel Structures, Improved Process For Making Capillary Channel Structures, And Extrusion Die For Use Therein," incorporated herein by reference. The Background section of the '248 patent additionally references a variety of alternative embodiments of approaches for forming fibers with surface channels or capillaries. In general, any of these approaches can be used. However, the fibers formed by the process of the '248 patent itself have desirable characteristics and versatility.

In some embodiments, the SCF fibers can also have shape memory. These fibers can be heated gently to cause the fibers to curl. The curled fibers can be stretched straight at room temperature. Upon heating to body temperature, the fibers resume the curled configuration. By using a bundle of the stretched fibers, the individual fibers of the bundle curl upon delivery due to body heat/hydration to form a fibrous filter mat that can entrap emboli within the fibrous network.

Since suitable fibers can be formed in a variety of ways, the cross sectional properties of the fibers can have similar variety. In some embodiments, the cross sectional properties of the fibers are relatively uniform along the length of the capillaries. The cross sectional properties can be considered as an average of the cross section along the length of the fiber with the surface capillaries. The cross section can be considered to have an outer perimeter that is formed by tracing along the outer surface of the cross section. In SCF fiber embodiments, due to the presence of at least one surface capillary, the outer contour of the perimeter of the cross section has at least one change in curvature. In some embodiments, the fiber has a plurality of surface capillaries with corresponding changes in curvature. Thus, a fiber can have a single surface capillary, two surface capillaries, or at least three surface capillaries, such as in appropriate embodiments from 3-25 surface capillaries as well as any and all values and subranges within this range.

The cross section can be characterized by a circumference that can be determined by magnifying the cross section, conceptually wrapping a tight string around the circumference, measuring the length of the conceptual string and scaling the length back according to the inverse of the magnification to obtain the circumference. Similarly, the area mapped out with this virtual string also characterizes the cross section of the fiber. The radius of the fiber can be estimated from the circumference if an overall circular shape is assumed since the circumference, c, can be related roughly to a radius, r, by the formula $c=2\pi r$. The capillaries themselves can be characterized roughly by their number, shape and wall thickness between the capillaries. Suitable wall thickness can depend on the size of the capillaries as well as the overall thickness of the fiber.

As with the fiber length, the thickness of the fibers can be selected appropriately for the particular use of the fiber. Fiber thickness can be measures in several ways. As described in the previous paragraph, the radius of the fiber can be roughly estimated from the assumption of a circular cross section. Alternatively, one can define an average diameter by taking an average cross section and then averaging the length of segments through the center of the cross section that intersect the circumference of the cross section. Also, calipers can be used to measure thickness, which can be averaged to obtain a value of the diameter. These various approaches at estimating the radius or diameter generally give values of roughly the same magnitude. Furthermore, in the fiber field, a pragmatic way has been developed to characterize fiber thickness without the need to resort to magnification of the fibers. Thus, fiber thickness can be measured in units of denier. Deniers correspond to the number of grams per 9,000 meters of yarn with a larger value corresponding to a thicker fiber.

In some embodiments, suitable fibers have diameters from 50 microns to about 5 millimeter, in further embodiments from about 100 microns to about 2 millimeters, and in additional embodiments from about 150 microns to about 1 millimeter. As measured in denier, SCF fibers can have sizes ranging from about 0.1 denier to about 1000 denier in size, in additional embodiments from about 0.5 denier to about 250 denier, in some embodiments from about 1.0 denier to about 200 denier, in other embodiments from about 2.0 denier to about 100 denier and in further embodiments from about 3.0 denier to about 50 denier. A person of ordinary skill in the art will recognize that additional ranges of fiber thickness in diameter measurements or in denier are contemplated and are within the present disclosure.

A capillary channel can have a width suitable for the particular application based on its function and its interaction with associated fluids. For many applications of interest, suitable capillary widths range from about 1 micron to about 0.5 mm (500 microns), in other embodiments from about 5 microns to about 250 microns, in further embodiments from about 10 microns to about 200 microns and in additional embodiments from about 25 microns to about 100 microns as well as all ranges and subranges within these. The width of a capillary channel can be evaluated from a measurement on a micrograph of fiber cross section based on the magnification, or it can be inferred from the die used to extrude the fiber if formed by extrusion. The width can be taken as the distance between the edges of the capillary along the circumference of the fiber such that the width corresponds with the surface opening of the capillary. A person of ordinary skill in the art will recognize that additional ranges of values of capillary widths within the explicit ranges are contemplated and are within the present disclosure.

Further characterization of the fibers can borrow from the approaches outlined in the '248 patent. In particular, the overall capillary sizes can be characterized. In some embodiments of interest, the fibers have a specific capillary volume of at least about 0.5 cc/g, in other embodiments at least about 1.0 cc/g, in further embodiments at least about 2.0 cc/g and in additional embodiments at least about 3.0 cc/g. Also, the specific capillary surface area can be at least about 500 $cm^2/g$, in some embodiments at least about 1000 $cm^2/g$, in further embodiments at least about 2000 $cm^2/g$, and in other embodiments at least about 3000 $cm^2/g$. A person of ordinary skill in the art will recognize that additional ranges of capillary volumes and capillary surface areas are contemplated and are within the present disclosure. Test methods for evaluating the specific capillary volume, the specific surface capillary area and the adhesion tension are described in detail in the '248 patent, which is incorporated herein by reference for the explicit description of the determination of these values.

In some embodiments, it is desirable for aqueous liquid, such as bodily fluids or components thereof to enter the capillaries. For these embodiments, the polymer properties and the capillary properties can be selected appropriately such that the capillaries can accept the liquid accounting for the surface tension of the liquid and the chemical properties of the liquid and the fiber. In particular, it can be desirable to provide for aqueous liquid entry into the capillaries for embodiments involving removal of particulates from a bodily fluid and for embodiments involving transport of biological liquids through the channels. For these embodiments, relatively hydrophilic polymers, such as polyesters, generally are suitable fiber materials for incorporating aqueous liquids into the capillaries.

While various capillary structures are covered herein, in some embodiments with high capillary volumes, the capillary walls can be particularly thin. If the capillary walls are thin, the capillary can collapse under compressive forces unless the polymer is resistant to compressive strain. Thus, in some embodiments, it is desirable for the polymers to have a modulus of elasticity of at least about 100 MPa and in other embodiments at least about 750 MPa at biological temperatures from about 35° C. to about 40° C. Similarly, the wetting properties of the polymer can be relevant. In some embodiments, the polymer has an adhesion tension with distilled water of at least about 20 dynes/cm and in further embodiments at least about 25 dynes/cm. With respect to the resulting capillary properties, the capillary structures in some embodiments exhibit a capillary sorption of at least about 1.5 cc/g at 5.0 cm capillary suction/hydrostatic tension with distilled water, in other embodiments at least about 4 cc/g at 5.0 cm and in further embodiments at least about 4 cc/g at 10 cm capillary suction. A person of ordinary skill in the art will recognize that additional ranges of modulus of elasticity, adhesion tension, and capillary sorption within the explicit ranges are contemplated and are within the present disclosure.

Test methods for evaluating the specific capillary volume, the specific surface capillary area and the adhesion tension are described in detail in the '248 patent, which is incorporated herein by reference for the explicit description of the determination of these values.

In general, the fibers can be attached together for incorporating into a device. For example, the fibers can be attached using chemical crosslinking, adhesives, twisting, weaving, heat bonding, or the like or combinations thereof Chemical crosslinking can involve the use of radiation or the like to activate the polymer to form chemical crosslinks and/or crosslinking agents that can bond with two or more polymer fiber elements. Suitable adhesives for bonding the fibers or a portion thereof are described in detail below. The fibers can be twisted or braided, for example using conventional approaches, to form a corresponding material. Weaving or similar physical association can be used to form structures for use in the device. In general, if formed from appropriate polymers, fibers or portions thereof can be associated together using heat bonding, which can be controlled to form desired fusing without inducing an undesirable loss of the fiber and surface channel structure. Furthermore, the fibers can be associated with additional materials or the like within the device to secure the fibers and or form the device.

The radiopaque polymers, whether or not composites, generally are selected to have desired physical properties. For fiber embodiments, the material generally should be flexible when formed into a fiber. In some embodiments, the material has a Shore Durometer D value of no more than 50 and in some embodiments no more than about 35D. While Shore Durometer values directly relate to hardness of the polymer, they correlate generally with flexibility and provide a convenient estimate of flexibility. Shore Durometer values can be measured using commercially available equipment. The radiopaque polymers can generally be formed into structures using conventional polymer processing techniques, such as molding, calendering, extruding and the like. Appropriate techniques can be used to form the desired device from the processed polymer. In particular, for the formation of fibers, extrusion can be particularly desirable. Suitable SCF fibers have been formed using extrusion with a loaded polymer composite.

The fibers can be extruded. To form fibers with a circular cross section, a die with a circular orifice can be used. Similarly, fibers with a non-circular cross section, such as an oval cross section, can be extruded with an appropriately shaped die. To extrude SCF fibers, the die orifice can be selected to produce the desired fiber geometry. However, upon cooling of the polymer after extrusion, the capillary walls tend to thicken and shrink in wall height. However, these effects can be adjusted for in the die design as noted in the '248 patent.

Commercial extruders are available for melt spinning thermoplastic polymers. Suitable spin lines are available, for example, from Davis-Standard, Pawcatuck, Conn. The loaded polymers can have a higher melt viscosity than the corresponding unloaded polymers. Thus, it may be desirable to alter the extrusion conditions, such as changing the extrusion temperature and/or increasing the pressure within the extruder. However, a person of ordinary skill in the art can adjust the extrusion conditions appropriately.

Figure 4:
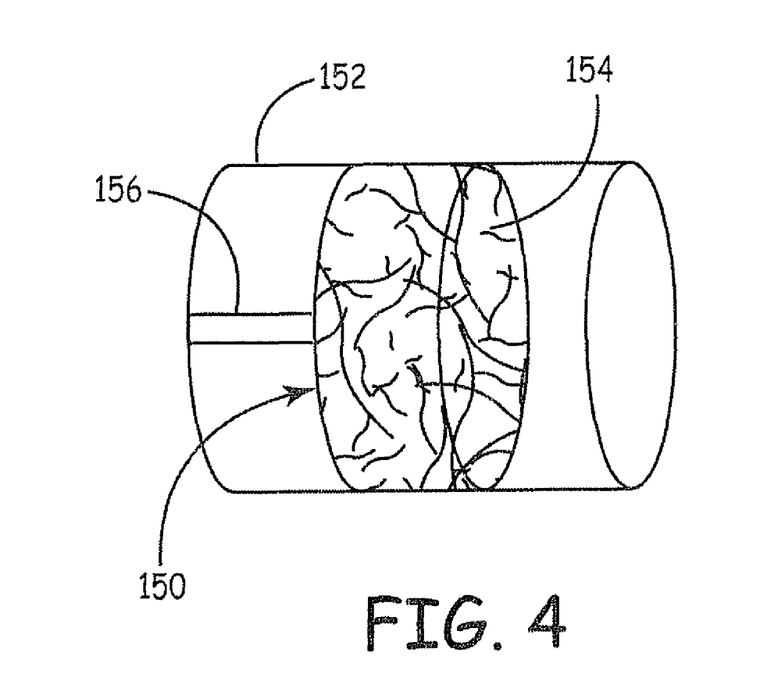
FIG. 4 is a schematic view of an embolic protection device within a patient's vessel in which the embolic protection device has a porous space filling three-dimensional polymeric filtration matrix comprising a radiopaque polymeric material.
Figure 5:
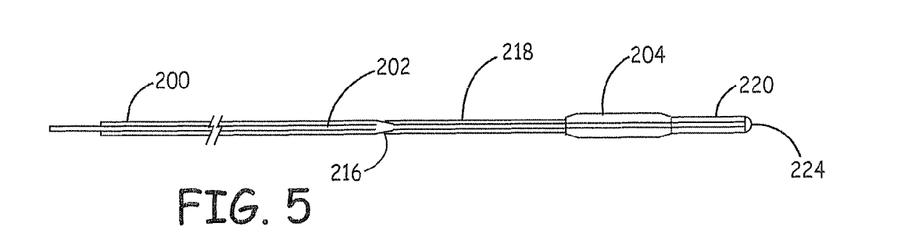
FIG. 5 is a sectional view of an embolic protection device with a fiber bundle comprising a radiopaque material in which the embolic protection device is shown in a low profile configuration suitable for deployment.

Furthermore, some embodiments of embolism protection devices are not fiber based. As noted above, filters with three dimensional filtration matrices can comprise various space filling polymeric structures. For example, the three-dimensional filtration matrix can comprise a space filling polymeric material, such as a hydrogel. The space filling polymeric matrix can be self-expanding, for example, due to absorption of liquid and/or through a structural memory. A representative space filling filter matrix is shown in FIG. 4. Filter 150 is shown deployed within a vessel 152. Filter 150 comprises a space filling polymer structure 154 forming a three-dimensional filtration matrix and a tether 156. Tether 156 can facilitate delivery and/or removal of the filter.

Hydrogels are generally hydrophylic polymers that are nevertheless not soluble in aqueous solutions. Generally, hydrogels are crosslinked to prevent them from being soluble. While they do not dissolve, the hydrogels swell with aqueous solution when in contact with the solution due to the hydophylic nature of the polymer. In additional or alternative embodiments, an expandable polymer can comprises a memory polymer that resumes a memory shape upon exposure to a stimulus, such as exposure to body temperature. In other embodiments, the expandable polymer can comprise a compressible polymer that expands upon release of a confining force such as the confinement provided by a sheath or the like. Furthermore, the embolism protection device can comprise additional polymers and/or other material to introduce desired properties to the device.

Thus, in some embodiments of interest, the devices have a component of a porous expandable polymer to fill the inner luminal space of the vessel. In addition, copolymers and/or polymer blends can be used in which one or more expandable polymers are combined with other monomer and/or polymer moieties to combine the properties of the different elements. For example, block copolymers, such as graft copolymers, can be used to combine polymer units into a combined material that incorporates properties of the respective polymers. Some embodiments of swelling copolymers can include, for example, hydrogels, which can expand large amounts upon contact with aqueous solutions.

Suitable hydrogels include, for example, crosslinked forms of polyacrylamide, poly(hydroxyethylmethacrylate) (PHEMA), cellulose derivatives, poly(vinyl alcohol) and polyethylene glycol. The degree of crosslinking, composition and other features can be used to control the degree of swelling. Some hydrogels can swell by a factor of 1000 percent or more upon contact with an aqueous solution. Several qualities of hydrogels have made them an attractive option in the medical device arena. These qualities include their ability to work as a protective barrier for open wounds and absorb excess fluids. In addition, hydrogels can be biocompatible, nontoxic, and nonthrombogenic, have inherent adhesiveness to tissue and have been shown to be capable of delivering drugs in a controlled fashion. Also, the hydrogels can be used to associate with other polymers that are less biocompatible or more thrombogenic to introduce desirable properties to the composite.

Suitable foam and sponge materials include, for example, polyester, aromatic vinyl polymers, polyether, polyurethane and mixtures thereof. Modified polyurethane polymers can be used to improve the biocomatability of the polymer. See, for example, U.S. Pat. No. 6,320,011 to Levy et al., entitled "Derivatized Polyurethane Compositions Which Exhibit Enhanced Stability In Biological Systems And Methods Of Making The Same," incorporated herein by reference. The foam/sponge materials can be formed, for example, in a molding process with a blowing agent. An example of a polymeric sponge material and methods of forming the sponge material are described further in U.S. Pat. No. 4,456,706 to Siedenstrang et al., entitled "Molding compounds, Sponge Articles Produced Therefrom And Process Of Production," incorporated herein by reference.

Compressible biocompatible polymers include, for example, foam products useful for biological applications. For example, hydrophilic polyether-polyurethanes and polycarboxylate polyurethanes can be used to form foam that is compressible while absorbing a large amount of aqueous solutions. U.S. Pat. No. 5,914,125 to Andrews et al., entitled "Wound Dressing," incorporated herein by reference, describes a hydrophilic polyether polyurethane foam material with an adsorptive capacity of at least about 10 times its own weight. In addition, published U.S. Patent Application 2002/0072550A to Brady et al., entitled "Biostable Polyurethane Products," incorporated herein by reference, describes foam materials with a void volume of 85% that are formed from either polyether polyurethanes or polycarbonate polyurethanes. In addition, polyurethanes poly-vinyl polymers can also be used to form biocompatible foams. U.S. Pat. No. 4,550,126 to Lorenz et al., entitled "Hydrophilic, Flexible, Open Cell Polyurethane-poly(N-vinyl lactam) Interpolymer Foam And Dental And Biomedical Products Fabricated Therefrom," incorporated herein by reference, describes a foam with a good ability to absorb aqueous fluids. These foams can be formed into appropriate shapes for use in the embolism protection devices described herein.

Fiber-Based Filter Elements

Filter elements of particular interest comprise, for example, fiber based three dimensional filtration matrices. As noted above, radiopaque fibers can be effectively used in embolism protection devices, and embolism protection devices with surface capillary fibers have been demonstrated to be very effective for filtration in human testing. A specific structure is described based on a bundle of fibers that are aligned for delivery into a vessel and bent into three dimensional filtration matrix for filtering.

In some embodiments of particular interest, the embolism protection device is placed at or near the distal end of an integrated guiding device. The integrated guiding device has a corewire within an overtube. Relative motion of the corewire and the tube can be used to deploy the embolism protection device from a confined narrow profile configuration for delivery to a deployed configuration at which the embolism protection device is expanded within the vessel. The actuation, which is generated by the longitudinal motion of the tube relative to the corewire, can release the embolism protection structure from a constrained environments, such as a sheath, as described further in published U.S. Patent Application 2004/0093015 to Ogle, entitled "Embolism Protection Devices," incorporated herein by reference, or can directly drive a reconfiguration of the device into a form that filters the lumen of the vessel, as described further in published U.S. Patent Application 2005/0085847A to Galdonik et al., entitled "Fiber Based Embolism Protection Device," incorporated herein by reference.

Figure 6:
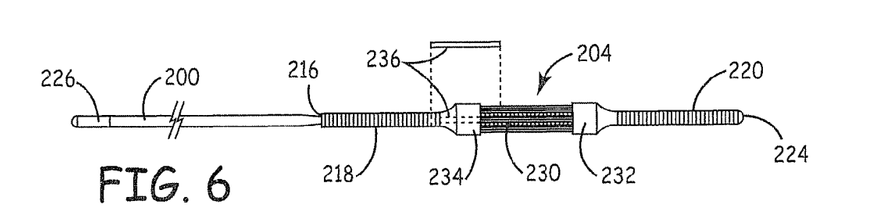
FIG. 6 is a side view of the integrated device of FIG. 5.
Figure 7:
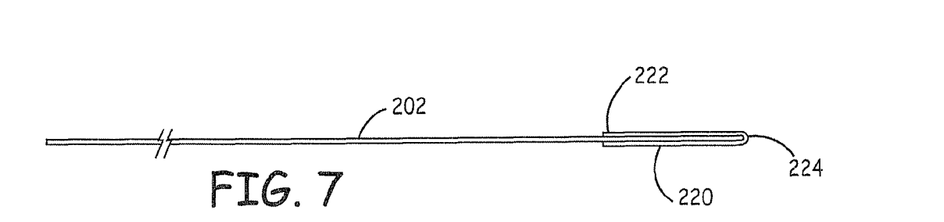
FIG. 7 is a side view of the corewire of the integrated device of FIG. 5.

One specific embodiment is shown in FIGS. 5-8. In this embodiment, the integrated guiding device comprises a tube 200, a corewire 202, and an embolism protection structure 204. Referring to the sectional view in FIG. 5 and the side view in FIG. 6, tube 200 has a tapered section 216 at its distal end that mimics the taper on a conventional corewire. A wire coil 218 extends from tapered section 216. Corewire 202 is covered with a coil 220 at its distal end, as shown in FIG. 7. Coil 220 is connected with solder 222 and a weld 224, although other attachment approaches can be used. Coil 220 and/or the tip of the weld can be made radiopaque to facilitate visualization for placement of the device into the patient. Grip 226 can be used to anchor the proximal end of corewire 202. Tube 200, corewire 202, wire coil 218, coil 220 and grip 226 can all be formed from stainless steel, although other suitable materials can be used.

In some embodiments, a back end tool can replace grip 226 to control more accurately the relative motion of corewire 202 and tube 200. In particular, a back end tool can have stops and/or markings to provide guidance on the extent of deployment of the embolism protection device. Furthermore, the rotational motion of the corewire can be coupled to the tube to provide for better steering of the device during placement within a vessel. Back end tools and torque coupling structures are described further in published U.S. Patent Application 2006/0200047A to Galdonik et al., entitled "Steerable Device Having a Corewire Within a Tube and Combination With a Functional Medical Component," incorporated herein by reference.

Figure 8:
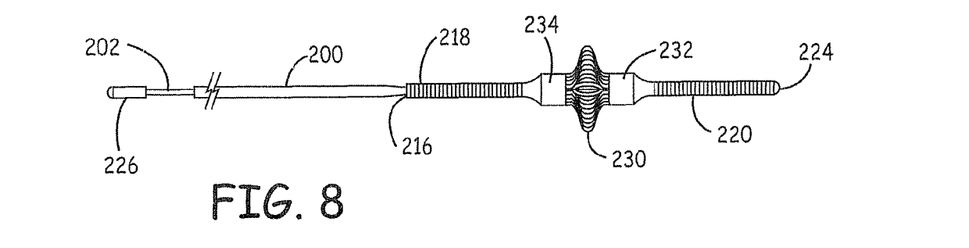
FIG. 8 is a side view of the device of FIG. 5 following expansion of the embolism protection device.

In the embodiment of FIGS. 5-8, embolism protection device 204 comprises a bundle of SCF fibers 230 attached at first attachment 232 and second attachment 234, as shown in FIGS. 6 and 8. Optionally, one or more tungsten or other radiopaque metal wires can be introduced into the fiber bundle along with the other fibers. A 0.1 inch long tube 236, which can be formed from polyimide polymer, is located within the second attachment 234 with corewire 202 extending with sliding freedom within the tube. The fibers are swaged/crimped at the two attachments 232, 234 to a diameter of 0.033 inches with bands, which may or may not be radiopaque. The bands can be made radiopaque so that the ends of the fiber bundles can be visualized during the procedure. An example of such an embodiment is shown below. The movement of the bands as they come together during deployment of the filter can similarly be visualized. After crimping, the fiber bundles are bonded at each end with an adhesive, such as cyanoacrylate. Alternatively or additionally, rather than crimping and or using adhesive, the fibers can be heat bonded together to anchor each end of the bundle with corresponding decreased risk of the fibers pulling out from the fastened end. Also, polymer bands, such as PET heat shrink, can be used to secure the bundle of fibers at the respective ends. This banding can be combined with any of the techniques discussed above.

The number of fibers in the bundle generally depends on the desired degree of filtration as well as the thickness of the fibers and the desired profile of the device for delivery. In general, the number of fibers can be range from at least 10 fibers, in further embodiments from 25 fibers to 1,000,000 fibers, in other embodiments from 50 fibers to 10,000 fibers and in additional embodiments, from 100 fibers to 5,000 fibers. The length of the fibers can be selected based on the size of the corresponding vessel. When deployed, the centers of the fibers are projected across the lumen of the vessel. Thus, the unconstrained length of the fibers between attachment structures 232, 234 should be at least double the radius of the vessel. In some embodiments relating to the use of a plurality of fibers to expand within the lumen of a patient's vessel, it is generally appropriate to use fibers that have a length from about 2.2 to about 10 times the vessel radius, in some embodiments from about 2.4 to about 5 times the vessel radius and in further embodiments from about 2.6 to about 4 times the vessel radius. For placement in a human vessel, the fibers generally have a length from about 0.5 mm to about 100 mm, in other embodiments from about 1 mm to about 25 mm, and in further embodiments from about 2 mm to about 15 mm. A person of ordinary skill in the art will recognize that additional ranges of fiber numbers and fiber length within the explicit ranges are contemplated and are within the present disclosure. In one specific embodiment, the device comprises 350 strands of 6 denier SCF fibers in a bundle and a crossing profile at delivery of 0.032 inches (2.4 French).

Visualization of Three-Dimensional Filtration Matrices

As noted above, the use of radiopaque materials in three dimensional filtration matrices can provide for both the identification of the position of the device within a vessel as well as the visualization of the contact of the filtration matrix with the vessel walls. Due to the nature of the three dimensional filtration matrices, the material of the filtration matrix can be constructed of a material that can contact the vessel wall without injuring the vessel wall. Also, the material can be deformable so that the filtration matrix can conform to irregularities of the wall. This ability to conform to the vessel wall and contact the vessel wall without damage provides for improved filtration since emboli cannot flow around the filter within the vessel. The ability to visualize the filtration matrix and the vessel wall provides the ability to verify the proper deployment of the filter in the vessel. This can be a significant advantage especially for procedures in the carotid artery, where any escaped emboli can cause stroke, and in the coronary arteries, where any escaped emboli can cause heart damage.

In general, the embolism protection devices are suitable for use in less invasive medical procedures in which a small incision is made to provide access to a vessel. The embolism protection device is then guided through the vessel to the desired location. The placement can be evaluated either with imaging, such as x-ray imaging, and/or with determination of the position based on the length of guiding device fed into the vessel. The use of x-ray imaging can provide confidence that the device has been placed in the correct location. The embolism protection devices are also useful in surgical procedures in which the blood vessel is exposed with an incision, if x-ray visualization is still useful to ensure proper deployment of the filter.

Once the embolism protection device is at a selected location, the device can be deployed by expanding the three dimensional filtration matrix or allowing the three dimensional filtration matrix to expand. As noted above, the filter can have a more intense x-ray image in the deployed configuration relative to the delivery configuration. More specifically, in some embodiments the filter has an x-ray image in its deployed with a peak intensity at least about 25% greater, in other embodiments at least about 30% greater and in further embodiments at least about 35% greater than the peak intensity of the x-ray image in its delivery configuration when the x-ray source is oriented perpendicular, i.e. at 90 degrees, to the axis aligned through the center of the vessel at the filter. A person of ordinary skill in the art will recognize that additional ranges of increased radiopacity within the ranges above are contemplated and are within the present disclosure. In general, for actual procedures the x-ray emitter is oriented at an angle from about 45 degree to about 135 degrees relative to the axis aligned along the center of the vessel. Based on this increase in image intensity, a health care professional monitoring the procedure can observe more easily the transition of the filter to its deployed configuration when observing the device in a video screen during real time imaging. Also, movement of marker bands on the integrated guiding device associated with the boundaries of the filtration matrix can be observed moving when the filter is deployed whether or not the filtration matrix itself is radiopaque.

The three dimensional filtration matrix in general is intended to contact the vessel wall and correspondingly conform to the wall through the contact. With the ability of the filter to adjust to contours in the vessel, all of the flow through the vessel passes through the filter. If the filter does not deploy properly, there may be gaps between the filtration matrix and the vessel wall that expose a passage for emboli to escape downstream from the filter. Therefore, it is desirable to visualize the deployed three dimensional filtration matrix in the vessel to determine the deployment of the filter. The vessel itself does not form an x-ray image, but contrast can be delivered into the vessel so that the position of the vessel walls can be inferred from the observation of the flow of the contrast. Thus, the proper deployment of the filter can be evaluated.

Figure 9:
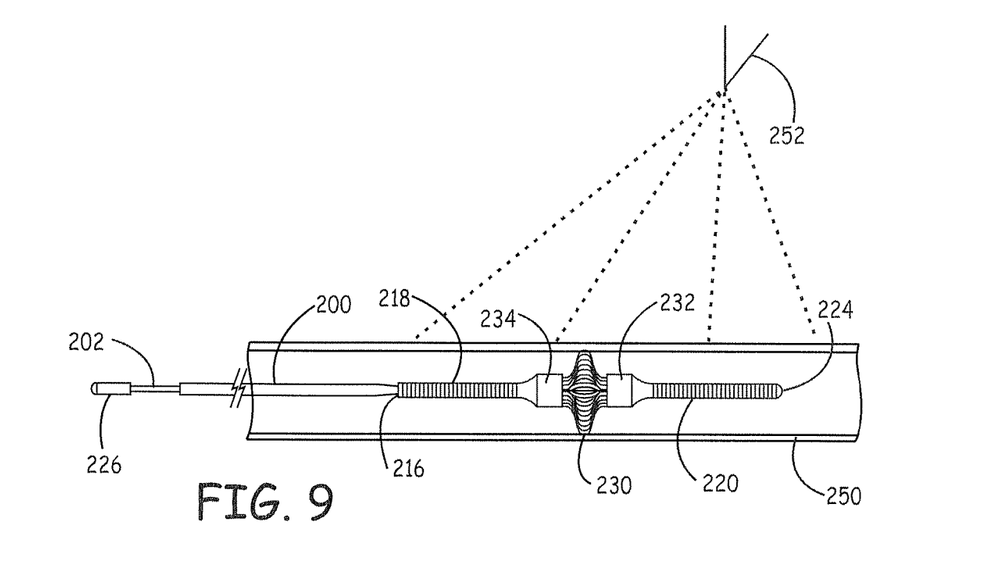
FIG. 9 is a schematic side view of a fiber-based embolism protection device deployed in a vessel.

Referring to FIG. 9, an embolism protection device of FIGS. 5-8 is depicted in a blood vessel 250. An x-ray source 252 can be used to generate an image. The image can be generated with an x-ray image intensifier and a video camera so that real time images can be viewed on a video screen during the procedure. Suitable systems for performing the imaging are described, for example, in U.S. Pat. No. 5,509,044 to Horbaschek, entitled "Medical Diagnostics System Having Optimized Signal Acquisition For Radiation Exposure Control," incorporated herein by reference.

Figure 10:
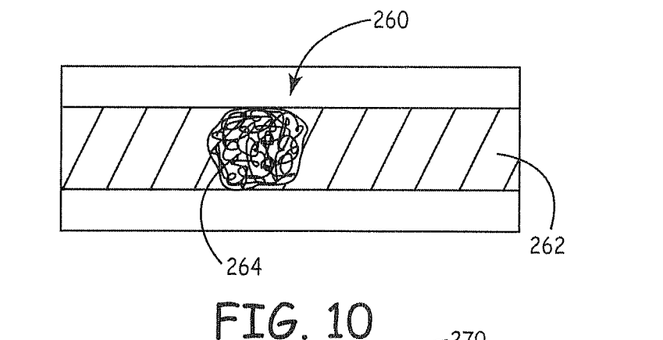
FIG. 10 is a schematic depiction of an image of a properly deployed filter with a three dimensional filtration matrix within a vessel.
Figure 11:
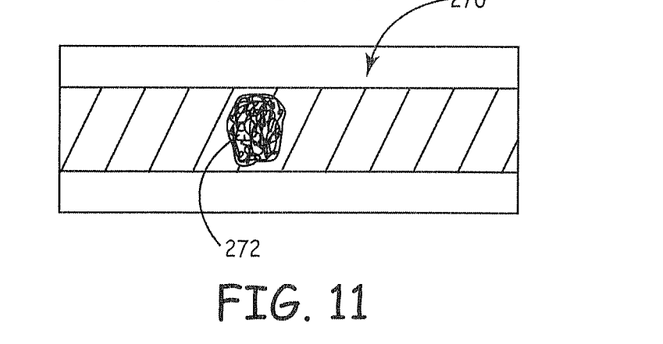
FIG. 11 is a schematic depiction of an image of an improperly deployed filter with a three dimensional filtration matrix within a vessel.

A representative image 260 showing the blood vessel 262 and the three dimensional filtration matrix 264 is shown in FIG. 10 for a properly deployed filter. The precise view depends on the relative orientations of the vessel and x-ray source. However, as shown in FIG. 10, the filtration matrix is shown with good contact with the vessel wall. In contrast, a representative image 270 for an improperly deployed filtration matrix 272 is depicted in FIG. 11. The image indicates that the filter is not deployed properly and that there are likely gaps between the filtration matrix and the vessel wall. While two dimensional imaging cannot ensure proper deployment of the filter, most significant improper deployments of the filter can be detected. Therefore, the safety of procedures protected with the three dimensional filtration matrices can be improved beyond the high levels already achieved with these filters. If desired, three dimensional imaging can be used to provide greater information on the filter deployment than is available from the two dimensional imaging, although this generally exposes the patient to greater amounts of x-rays.

If an improperly deployed filter is observed in the image, the filter can be undeployed and redeployed by moving the corewire relative to the overtube. Observation of the image can evaluate whether or not the redeployment of the filter corrected the contact with the vessel wall. Alternatively, the filter can be removed and replaced. In particular, if one or a few attempts to redeploy the filter are similarly unsuccessful, generally the filter would be replaced.

EXAMPLE

This example describes the ability in a model system to visualize a fiber-based embolism protection device formed with radiopaque fibers. Animal studies were performed with the filter in a dog model, and in vitro studies were also evaluated using bags of saline to model body mass.

The embolism protection device was similar to the structure shown in FIGS. 5-8. The filter had 350 strands of 6 denier, 4DG™ SCF fibers in a bundle. The fibers were polyester loaded with 20 weight percent of bismuth subcarbonate with an average particle size of roughly less than five microns. The composite material was extruded to form the fibers.

Figure 12:
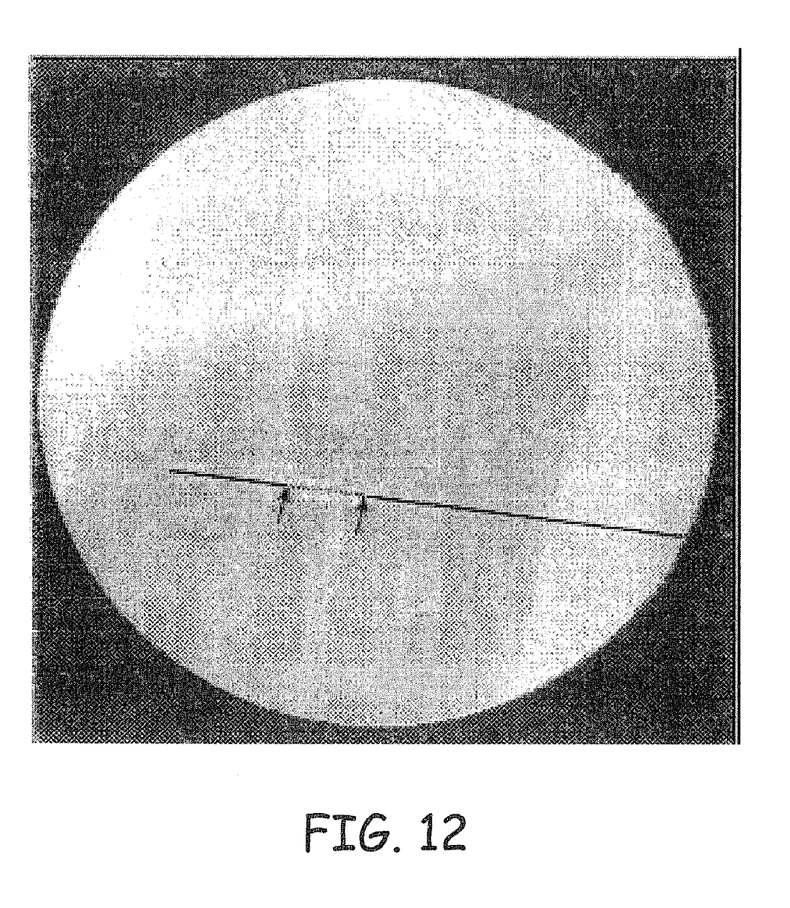
FIG. 12 is a picture of an x-ray image of an embolism protection device within a polymer tube modeling an artery with saline bags used to model body mass, in which the filter element is depicted in its delivery configuration and arrows point to radiopaque maker bands near the edges of the filter element.
Figure 13:
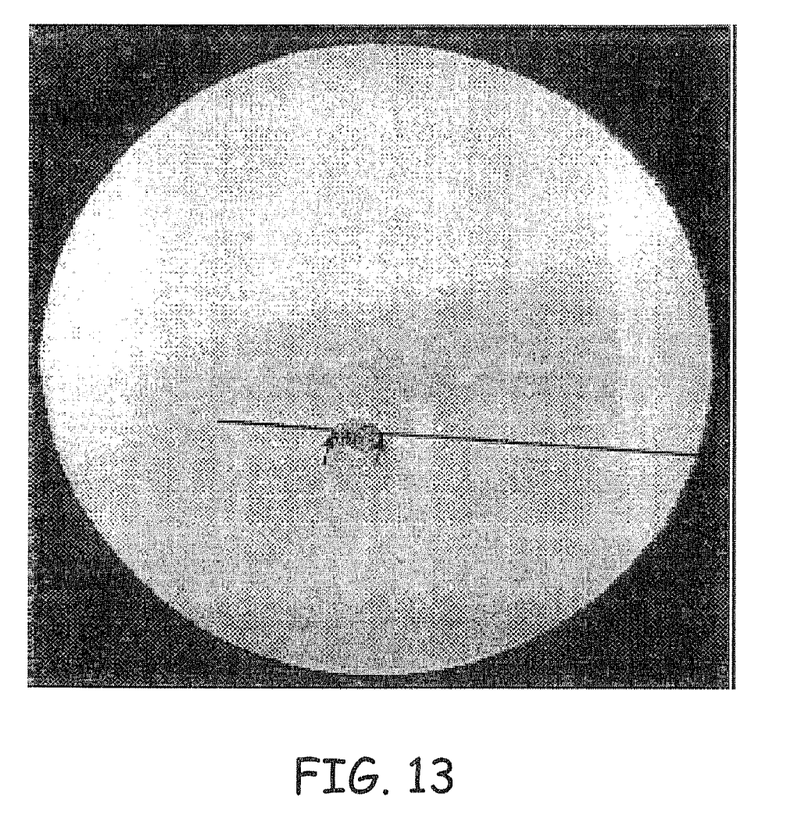
FIG. 13 is a picture of an x-ray image of the embolism protection device of FIG. 12 in which the filter is in a deployed configuration with arrows pointing to radiopaque marker bands and a line is drawn around the image of the three dimensional filtration matrix.

The visualization was performed using conventional surgical equipment. Saline bags were used to model body mass. A polymer tube of known diameter was used to model an artery. The filter element was reasonably clear in video observation using contrast. Still photos are shown in FIGS. 12 and 13. The guide structure is visible in the photos as a thin line. FIG. 12 depicts the filter in a delivery configuration prior to deployment of the filter. Arrows point to marker bands where the respective ends of the fibers are attached to the guide structure. FIG. 13 depicts the filter in a deployed configuration. Note that the marker bands are closer together in FIG. 13 relative to the picture in FIG. 12. The image of the filter element is roughly encircled in FIG. 13. While the images are clearer in a video presentation, the still photos provide evidence of the ability to visualize the filter element.

The embodiments above are intended to be illustrative and not limiting. Additional embodiments are within the inventive concepts. Although the present invention has been described with reference to particular embodiments, workers skilled in the art will recognize that changes may be made in form and detail without departing from the spirit and scope of the invention. The incorporations by reference above are intended to incorporate the full disclosures of the references to the extent that the incorporated subject matter is not inconsistent with the explicit disclosure herein, which will not be altered by any incorporation by reference, as well as the disclosures with respect to the specific issues referenced in the incorporation.

What we claim is:

1. A medical device for deployment inside a vessel comprising a radiopaque filter element comprising a plurality of fibers having a delivery configuration with a low profile relative to a longitudinal axis having a first peak radiopacity and an extended configuration with the fibers forming a three dimensional filtration matrix having a large profile relative to the longitudinal axis having a second peak radiopacity, wherein the second peak radiopacity is visibly greater than the first peak radiopacity, wherein the fibers are polymer surface capillary fibers with at least one channel that extends substantially parallel to the length of the polymer surface capillary fiber and along at least a portion of the length of the polymer surface capillary fiber, and wherein the filter element further comprises an unwoven combination of polymer surface capillary fibers and one or more radiopaque metal wires or polymer surface capillary fibers with a radiopaque metal coating, or a composite polymer surface capillary fiber structure of polymer and radiopaque inorganic particles, said medical device further comprising an integrated guide structure comprising an overtube and a corewire extending within the overtube, wherein one end of the fibers in the bundle is operably connected to the corewire and a second end of the fibers is operably connected to the overtube, the relative movement of the overtube and corewire resulting in a transition of the filter element between the delivery configuration and the extended configuration.

2. The medical device of claim 1 further comprising a tether operably connected to the filter element.

3. The medical device of claim 1 wherein the filter element comprises the polymer surface capillary fibers comprising a polymer with a radiopaque coating.

4. The medical device of claim 1 wherein the filter element comprises an unwoven combination of polymer surface capillary fibers and one or more radiopaque metal wires.

5. The medical device of claim 1 further comprising radiopaque marker bands located near the respective ends of the fiber bundle.

6. The medical device of claim 1 wherein the filter element comprises a composite polymer surface capillary fiber structure of a polymer and radiopaque inorganic particles.

7. The medical device of claim 6 wherein the composite comprises at least about 15 weight percent inorganic particles and wherein the inorganic particles are radiopaque.

8. The medical device of claim 1 wherein the filter element comprises about 2 weight percent to about 40 weight percent of radiopaque material.

9. The medical device of claim 1 wherein the second peak radiopacity of the deployed configuration is at least 25% greater than the first peak radiopacity of the delivery configuration.

* * * * *